United States Patent [19]

Millet et al.

[11] Patent Number: 4,834,076
[45] Date of Patent: May 30, 1989

[54] DEVICE FOR TREATING THE EXTERNAL HUMAN EPITHELIUM, PROCESS FOR ITS MANUFACTURE AND PROCESS FOR USING SUCH A DEVICE

[76] Inventors: Jean M. Millet, 39, Boulevard de Cimiez, 06000 Nice; Christian Chapoton, 10, rue de la Grande Truanderie, 75001 Paris, both of France

[21] Appl. No.: 852,365

[22] Filed: Apr. 15, 1986

[30] Foreign Application Priority Data

Apr. 17, 1985 [FR] France ............... 85 05820

[51] Int. Cl.4 ............... A61H 7/00; A61H 11/00; A47K 7/02
[52] U.S. Cl. .................. 128/65; 15/104.93
[58] Field of Search .............. 128/65; 401/268; 15/104.93, 104.94; 604/289, 290

[56] References Cited

U.S. PATENT DOCUMENTS

| | | | |
|---|---|---|---|
| 1,960,192 | 5/1934 | Howard | 15/104.93 |
| 2,007,107 | 7/1935 | Bottrill | 128/65 |
| 2,090,050 | 8/1937 | Jackson | 128/65 |
| 2,670,489 | 3/1954 | Cross et al. | 15/104.93 |
| 3,150,049 | 9/1964 | Emory | 15/104.93 |
| 3,624,224 | 11/1971 | Watchung | 15/104.93 |
| 3,795,624 | 3/1974 | Feinstone | 15/104.93 |
| 3,810,841 | 5/1974 | Richter | 15/104.93 |
| 3,978,204 | 8/1976 | Charlé et al. | 15/104.93 |
| 4,188,447 | 2/1980 | Ehlenz | 15/104.93 |
| 4,189,395 | 2/1980 | Bland | 15/104.93 |
| 4,203,857 | 5/1980 | Dugan | 15/104.93 |
| 4,206,196 | 6/1980 | Davis | 15/104.93 |
| 4,323,656 | 4/1982 | Strickman et al. | 15/104.93 |
| 4,346,493 | 8/1982 | Goudsmit | 15/104.93 |
| 4,397,754 | 8/1983 | Collishaw et al. | 15/104.93 |
| 4,469,094 | 9/1984 | Kaeser | 128/65 |
| 4,559,157 | 12/1985 | Smith et al. | 15/104.93 |
| 4,685,423 | 8/1987 | Baker et al. | 15/104.93 |

OTHER PUBLICATIONS

The Condensed Chemical Dictionary, Tenth Edition, Editor Gessner Hawley, 1981, publisher Van Nostrand Reinhold Co.

*Primary Examiner*—Edgar S. Burr
*Assistant Examiner*—Kimberly L. Asher
*Attorney, Agent, or Firm*—Browdy and Neimark

[57] ABSTRACT

A device designed for treating the external human epithelium comprising a rigid slow-release impregnated macromolecular matrix carrying a suitable active substance, the matrix releasing very small and controllable discrete quantities of the substance upon being pressed by massaging or rubbing against the epithelium. The active substance may comprise a combination of active agents such as vitamins and unsaturated fatty acids.

17 Claims, 1 Drawing Sheet

DEVICE FOR TREATING THE EXTERNAL HUMAN EPITHELIUM, PROCESS FOR ITS MANUFACTURE AND PROCESS FOR USING SUCH A DEVICE

The invention relates to a device for treating the external human epithelium, the process for its manufacture and a process for using such a device.

It relates especially to a device of this type which is particularly suitable for treating the constituent epithelial tissue of the facial skin and/or the scalp and also, if appropriate, certain superficial body growths such as hair.

The invention also relates to a process for the manufacture of such a device.

The invention further relates to a process for using a device of this type which is capable of being employed for example for conditioning the hair or for transferring and/or delivering hygienic, cosmetological or similar active substances to the epidermis, in particular to the sensitive areas of the skin, such as the facial skin.

Patent document FR-A-No. 2 385 392 has already disclosed a hair conditioning process in which the hair is rubbed with an article consisting of a flexible support with which a normally solid hair conditioner is releasably associated, for transferring an effective quantity of the conditioner to the hair. The flexible support is in the form of a piece of paper, fabric or the like and requires the hair to be wetted before being rubbed with the said article. The process described is thus inconvenient to carry out, or at least impossible to carry out other than in a bathroom, so its use is necessarily restricted.

Patent document GB-A-No. 632 544, for example, has also disclosed a comb for treating or dyeing the hair, which is made of a water-soluble, chemically inert, synthetic polymeric compound in which a dyeing or bleaching substance or a perfume which is soluble in water is incorporated. A device of this type has the same disadvantages as those associated with carrying out the process referred to above.

To overcome these disadvantages, combs of the type described in Patent document GB-A-No. 413 767 or U.S. Pat. No. 2,154,822 have also been proposed which carry, on their teeth, a product which can be deposited on the hair, for example from a fine impregnated tuft fixed to some of the teeth of the comb, in the British patent, or from a waxy compound placed on the teeth, in the American patent.

In addition to these known devices and in a totally different field, a process has already been proposed for combatting ectoparasites on an animal, in which its coat is brushed or combed using an article with projecting parts, at least some of which are made of a polymeric material comprising a pesticide which can be level with the surface of the article: EP-A-No. 0,122,605. The insecticide deposited on the hair is inhaled or ingested by the ticks, fleas or other ectoparasites, which move in the animal's coat until they have received the lethal dose, which eliminates them. The device is not intended to bring an active substance into contact with the animal's delicate skin, but to place the desired insecticide in the dense coat, which comprises three types of hair, namely underfur, whiskers, and overhair.

Against the background of this very heterogeneous state of the art encompassing objects as diverse as combs according to the British patent, towels according to the French patent or brushes for dogs according to the European Application, the Applicants set themselves the problem of providing a device for treating the external human epithelium, in particular the facial skin, the scalp and the hair, which would make it possible to take effective action against certain pathological disorders of this epithelium, for example the appearance of wrinkles, hair loss, the appearance of dandruff, psoriasis, seborrhea and other phenomena associated with aging, and also for carrying out a cosmetological treatment, especially on the face and the hair.

Moreover, the Applicants endeavored to solve the said problem by means of a device which would be as simple as possible to use, which would involve this device only, which would not require metering, which could be used with simple and conventional movements and which, as a further feature, would not be in a liquid or viscous form like some of the known creams or lotions, so that the application and transfer of active substance(s) to the epithelium to be treated could be envisaged by means of repeated applications each providing a small or very small quantity.

In an attempt to provide a solution to the said problem, the Applicants considered using the slow-release matrix polymer systems which have been developed for many years for the transdermic administration of medicinal substances. The experiments undertaken along these lines proved unsuccessful, however, the known devices, intended for permanent application to the epidermis, being totally unsuitable for repeated but intermittent use on the facial skin or the scalp. In fact, whereas transdermic devices for applying medicinal substance(s) are required to have flexible forms, such as bands or bracelets capable of deforming with the movements of their users, combing or brushing devices or the like, on the other hand, are required to be resistant for prolonged use and rigid so as to withstand without deformation the relatively large forces to which they are subjected when used on human hair. This also results in differences in the methods of manufacture. In fact, if it is desired to increase the rigidity of a polymer matrix, for example by reducing the quantity of plasticizer which is generally associated with it in the known devices, the molding process can no longer be carried out under the conditions known for the abovementioned devices for transferring medicinal substances; the manufacturing temperature has to be increased, but if the temperatures employed in the manufacture of conventional plastic brushes or combs are reached, these are very considerably higher than the temperature at which the active agents which could be used are destroyed.

Surprisingly, the Applicants have now established that, with a suitable choice of matrix-forming polymers and the active substance or substances, as well as adjuvants, it is possible to provide a device for treating the external human epithelium, in particular certain sensitive areas of the skin, such as the facial skin and the scalp, and/or the hair, which satisfies the conditions stated above. As used herein, the term "rigid" means that the device essentially fails to deform when brushed, combed or otherwise contacted to release the active substance to the desired area.

In a device according to the invention for treating the external human epithelium, in particular sensitive areas of the skin, such as the facial skin and the scalp, and/or the hair, with an object which is intended to come into contact with the epithelium and/or its superficial growths in order to deposit an active substance thereon, the said object, in the shape of an article for massaging the skin or in the shape of a hair styling instrument, consists, at least in its parts which are intended to come into contact with the skin and/or the scalp and/or the hair, of a rigid macromolecular matrix incorporating at least one active substance chosen for its therapeutic and/or cosmetological action and for being releasable near the external surface of the said matrix, from which it is removed by massaging and/or contact and/or rubbing with the skin, the scalp and/or the hair.

In one embodiment, the massaging article or hair styling instrument, in the shape of a comb, brush, slide, curler, roller, pin, clip or the like, comprises a rigid frame to which the macromolecular matrix incorporating the active substance or substances is fixed.

In another embodiment, the parts which are intended to come into contact with the skin and/or the scalp and/or the hair, and which are made of the reinforced or non-reinforced macromolecular matrix, form an assembly fixed in a detachable or non-detachable manner to a handle, grip or the like, which is made of a different material from that of the macromolecular matrix.

According to the invention, the active substance contained in the latter is chosen to contain one or more agents with a therapeutic and/or cosmetological action which are active in skin treatment, in particular treatment of the phenomena associated with aging, such as wrinkles on the face.

In yet another embodiment, the active substance or substances is (are) chosen from those containing one or more agents which are active in treating hyperseborrhea, psoriasis, hair loss or dandruff or in assisting fresh hair growth.

In one other embodiment, the active substance or substances is (are) chosen from those containing one or more cosmetically active agents for facilitating styling, disentangling, conditioning, cleaning and modification of the texture, color and/or appearance of the hair.

According to another characteristic of the invention, the active substance or substances acts (act) as a plasticizer for the macromolecular matrix.

In one embodiment, the active substance contains one or more vitamins and/or unsaturated fatty acids.

In another embodiment, the active substance contains from 1 to 25% of plant and/or animal extracts and/or essential vegetable oils.

In a preferred embodiment, the active substance contains one or more ingredients favoring the transcutaneous passage of the active agents.

In an advantageous embodiment, the matrix contains from 3 to 25% of pyrithione or its derivatives as the active agent.

In yet another embodiment, the matrix contains from 1 to 25% of coal tar or its derivatives as the active agent.

A device according to the invention thus makes it possible to spread one or more active agents over the facial skin and/or the scalp and, if appropriate, the hair with simple movements, without using products other than the device, without the need for metering and without having to use cream, lotion or the like.

It also makes it possible to increase the frequency of treatment, this being an essential factor in the therapeutic result, while at the same time eliminating the rebound effects known with other methods of application, i.e., for example, the reappearance of dandruff to an increased degree a few days after shampooing, even though it partially disappeared immediately after shampooing.

If the device is in the form of a brush, the active substance is distributed each time the skin is massaged or each time the hair is styled (brushed or combed) deep down and in contact with the scalp, ensuring that the latter is massaged.

Of the numerous embodiments of the device according to the invention, a preferred form is that of a wand of which at least the end, which is flattened or toothed, is made of the active matrix, so that the wand can be used as an applicator of active substance by massaging the skin and/or the scalp.

In the case of the other hair styling instruments, the active substance released and then removed by rubbing (especially with the hair) gradually migrates into the hair and reaches the scalp, remaining in a sufficient quantity to be active by virtue of the customary frequency with which these instruments are used.

According to another important characteristic of the present invention, the active substance does not leave the facial skin, the scalp and/or the hair covered with grease or powder.

Good results have been obtained with devices according to the invention in the treatment of the facial skin and/or the scalp and/or the hair, notwithstanding the relatively acidic character of this external human epithelium and its substantial covering of lipids, the quantities of active substances released at their sites of action being appreciably smaller than those used in the conventional methods of application.

The invention also relates to a process for the manufacture of a device such as described above, wherein a dry powder is prepared by mixing one or more constituent polymers of the matrix, at a temperature of about 60°, with one or more active agents which has (have) been micronized beforehand if it (they) is (are) in the solid form, or microsolubilized in a mixture of plasticizer and adjuvants, the said powder is left to cool and ingredients such as perfumes or the like are then added, and the device is shaped by molding or extruding at a temperature of between 80° and 140° C. in a mold of appropriate shape. The active agent, once mixed or dissolved in a carrier, becomes an active substance.

In a modified method of carrying out the process, some active agents are solubilized in an organic solvent prior to being mixed with the plasticizer or plasticizers, the adjuvant or adjuvants and the macromolecular matrix, in order to improve the homogeneity and favor the release of the active substance from the finished device.

The relatively low molding or extrusion temperature, which enables degradation of the active substance or substances to be avoided, is made possible by a suitable choice of matrix formulations and by carrying out the extrusion or molding at a slower rate than normal.

In the case of injection molding, the material stays in the cylinder longer before injection, so as to be brought to the molten state at a homogeneous temperature before being forced into the cavities of the mold having the configuration of the active parts, such as the teeth of combs or brushes, of the hair styling instruments, or only parts of these devices, for example the teeth in the case of a comb.

In one method of carrying out the process, the shaping operation by molding or extrusion only involves the active parts of the device, which are then fixed, if required, to a support such as a handle or grip, which is made of the same material as that forming the matrix, but without active substance, or a different material.

In a modified method, the active and non-active parts are shaped simultaneously.

To obtain the requisite rigidity of the device according to the invention, provision is made to limit the quantity of plasticizer contained in the matrix to values of between 0 and 25% by weight of the matrix in the case of active agents with plasticizing properties, the polymer or polymers representing about 45 to 90% by weight of the matrix, depending on the active substance used.

In a modified method, the molding or extrusion of the active parts of the device takes place on a frame made of plastic or other suitable material.

The process step in which the agent is micronized if it is in the solid form, or microsolubilized if it is in the liquid form, prior to being mixed with the constituent ingredients of the matrix, makes it possible to ensure a satisfactory release of the active substance near the surface of the matrix, having regard to the efficacy of the active agent or agents making up the active substance, which is incorporated in the matrix in a proportion of 2 to 25% by weight.

The invention also relates to a process for using a device such as described above for applying, to the external human epithelium, in particular the sensitive areas of the skin, such as the facial skin and the scalp, and/or the hair, one or more active substances for combatting aging and/or pathological conditions of the said epithelium and/or for conditioning its superficial growths, wherein the said deposition results from repeated massaging, contact and/or rubbing, spaced out over a period of time, on and/or with the areas to be treated, with a device consisting of a macromolecular matrix in which at least one active substance is incorporated, the said substance being releasable near the surface, from which it is removed by the said massaging, contact or rubbing. The process according to the invention can be used to treat disorders of the skin and/or the scalp and the hair, including phenomena associated with aging, namely wrinkles on the face and hair loss, in particular dandruff.

In the case of combatting wrinkles on the face or other sensitive areas of the skin, the application of the active substance is associated with massaging at the same time as the release of active substance, which it favors. Any risk of applying an overdose of the said substance is excluded because of the fact that the slow release of the said substance from the matrix requires a certain time for the concentration at the periphery and on the surface of the said matrix to return to its level before the massaging started.

In this kind of use, the active substance advantageously comprises nutrients such as vitamins, biological plant or animal extracts like hormones, essential oils, tissue extracts or derivatives of the substances forming the intercellular matrix of the dermis.

If the process is intended to treat the scalp and the hair, its main purpose is to combat dandruff, seborrhea, psoriasis or hair loss or to assist fresh hair growth.

In this case, the active substance advantageously comprises tars or tar derivatives such as coal tar, mineral or vegetable oils or alternatively pyrithiones and their derivatives, unsaturated fatty acids, etc.

If the process is used to condition the hair for cosmetic or hygienic purposes, i.e. styling, disentangling, fixing, cleaning or modifying the texture, color or appearance of the hair, the active substance advantageously contains a grease absorber such as orris or lycopodium powder, a detergent or silicone oligomers, fatty acid derivatives, quaternary ammonium compounds, etc.

Advantageously, the invention also envisages combining active substances of both types, such a combination having a synergistic effect to give a device with both therapeutic and cosmetic effects.

The invention will be clearly understood from the following description given by way of example and with reference to the attached drawing, in which.

Figure 1A:
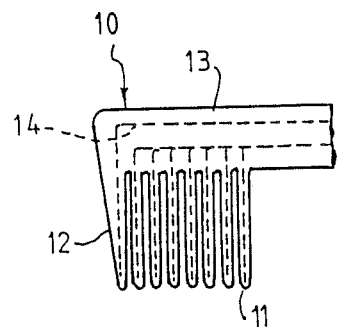
FIGS. 1A and 1B are schematic views of embodiments of a device according to the ivnention.
Figure 1B:
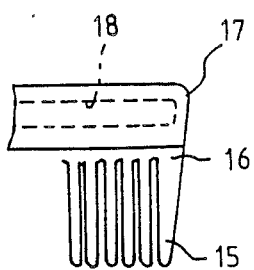

Reference is made first of all to FIG. 1, which schematically shows various embodiments of a device according to the ivnention.

In a first embodiment, (FIG. 1A) the device is in the form of a comb with teeth 11, which consists of a macromolecular matrix incorporating an active substance which can be released near the external surface 12 of the teeth when the comb is passed through the hair. In the embodiment illustrated in FIG. 1A, the teeth 11 and the body 13 are shaped over a frame 14, shown in broken lines, which also comprises a body and teeth made of a material of greater rigidity than that forming the macromolecular matrix, whereas in FIG. 1B, the teeth 15 and their base 16 are shaped into an assembly with no frame, which is integrally made of the said macromolecular matrix and then fixed to a body 17 with or without a frame 18. This last embodiment enables the use of active substance to be restricted to only those parts, such as the teeth 15, which are intended to come into contact with the hair and/or the scalp, thus making it possible to reduce costs and also to avoid the deposition of active substance on the user's hand, which does not have to be treated.

Figure 2:
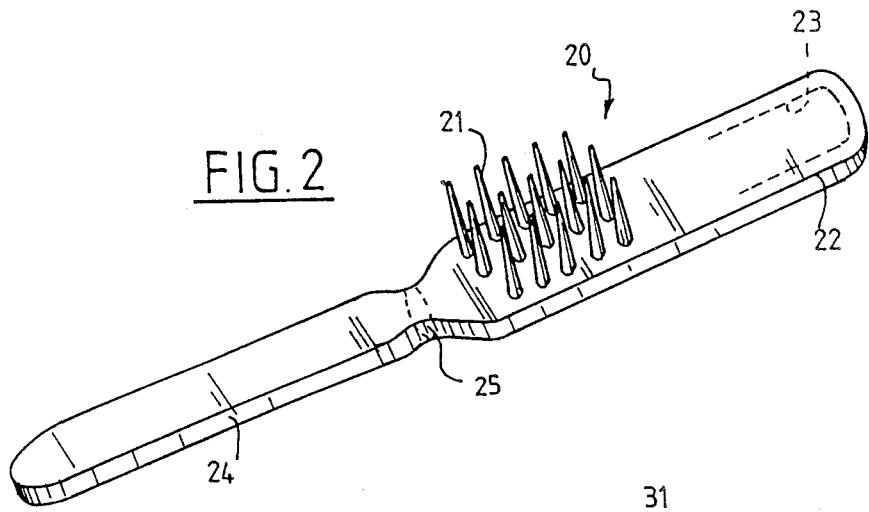
FIG. 2 is a schematic view in perspective of another device according to the invention.

In the embodiment shown in FIG. 2, the device is shaped into a brush 20 with teeth 21, which forms, together with the body 22, an assembly made of a macromolecular matrix incorporating at least one active substance which can be released near the surface of the teeth, from which it is removed by rubbing. In this embodiment too, the body 22 is advantageously molded over a frame 23, which is intended to give the assembly the requisite rigidity, and the body 22 is joined to a handle or grip 24, which can be integral with the body 22 or detachably joined thereto. Irrespective of the method of joining, and in the case where the grip 24 is also made of a polymeric material, provision is made to create the junction 25 between the body 22 and the grip or handle 24 with the smallest possible section in order to prevent phenomena of interdiffusion between the macromolecular matrix, incorporating active substance, and the constituent material of the handle or grip.

Figure 3:
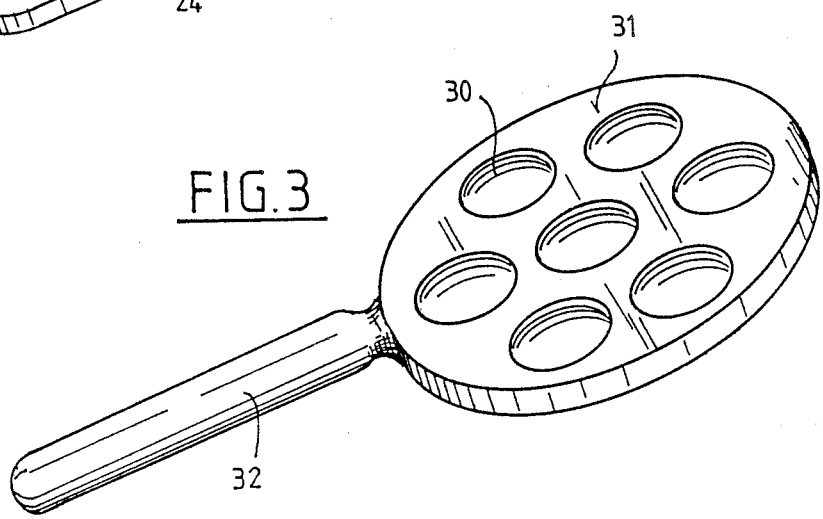
FIG. 3 is a schematic view, also in perspective, of yet another device.

In the embodiment shown in FIG. 3, the device is in the shape of a massaging article with beads 30 made of a macromolecular matrix incorporating an active substance which can be released near the surface, from which it is removed by contact with the areas of the skin to which the article is applied. In this embodiment, the beads 30 are mounted to rotate freely in a body 31 fixed to a grip or handle 32, the body 31 and/or the grip 32 advantageously being made of materials other than those forming the macromolecular matrix, or of the same material but without active substance.

Whatever the embodiment of the device according to the invention and the process for its manufacture, provision is made to pack it in a leaktight form of packaging from which it is removed when used for the first time, after which it can then be used for a period of the order of 4 weeks to a few months, depending on the active substance released and the formulation of the matrix.

The latter is chosen according to the active substance to be incorporated therein and is preferably made up of a synthetic organic polymer or a mixture of such polymers, a natural polymer (biopolymer) or a mixture of such polymers, inorganic polymers, synthetic polymers or synthetic elastomers.

Examples of macromolecular substances which can be used according to the invention are polyolefins (for example polyethylene, polypropylene, ethylene/propylene copolymers), polyacrylates (for example polymers and copolymers of methyl acrylate, ethyl acrylate, methyl methacrylate, ethyl methacrylate), polymers of vinyl compounds (for example polystyrene or polymerized divinylbenzene), polyvinyl esters, polyvinyl halides (polyvinyl chloride), polyvinyl acetates (for example polyvinylbutyral), vinylidene compounds (for example polyvinylidene chloride), ethylene/vinyl acetate copolymers, synthetic and natural elastomers (rubber obtained from hevea brasiliensis, cis-4-polyisoprene, polybutadiene or SBR, SBS, SEPS, CEPC or CEBC rubber), urea/formaldehyde and melamine/formaldehyde resins, epoxy resins (for example polymers of polyglycidyl ethers of polyhydric phenols), cellulosic plastics (for example cellulose acetate, cellulose phthalate, cellulose butyrate, cellulose nitrate) and polyurethanes.

It is also possible to use other natural resins such as paraffins, or other synthetic polymers such as polyvinyl alcohols, polyacrylamide, polyethers, polyamides, polyureas, polyacrylonitrile and polymethyl methacrylate.

The macromolecular matrix generally comprises one or more plasticizers, although this is not always necessary.

The invention can be carried out using conventional plasticizers, for example phthalates such as dibutyl phthalate and dioctyl phthalate, sebacates, for example dipentyl sebacate and dibenzyl sebacate, adipates, for example dioctyl adipate and dibutyl adipate, plasticizers of the hydrogenated polyphenol type, alkylated aromatic hydrocarbons and plasticizers of the polyester type, such as polyesters of polyols, for example hexanediol, or of the carboxylic acid type, such as sebacic or adipic acid.

In the case of active substances such as defined below, incorporating active agents with plasticizing properties, the said agents are used as both active agent and plasticizer, by themselves or in association with a customary plasticizer, the latter then being in a smaller quantity than usual. It is therefore possible to incorporate a larger quantity of active substance in the device and to preserve sufficient rigidity.

If appropriate, the matrix also comprises other adjuvants such as stabilizers, antioxidants, fillers, lubricants, mold release agents, antistatic agents, colorants or perfumes.

The active substance is chosen for its properties in treating the external epithelium and/or its superficial growths, for example the facial skin and/or the scalp and/or the hair, and for its ability to be incorporated into the matrix, to be released and to be removed therefrom by massaging and/or contact and/or rubbing with the facial skin, the hair and/or the scalp.

The active substance is advantageously chosen from those having one or more of the following actions: antifungal, antibacterial, antiseptic, antiseborrheic, keratolytic, antiinflammatory, antipsoriatic, antipruriginous, cicatrisant, antidandruff, nutritive and hormonal, or favoring hair growth.

Other active substances are chosen for their cosmetic or cleaning properties.

In a first particular embodiment of the invention, the active substance gives the device an antidandruff, antiseborrheic and/or antipsoriatic action.

In this case, it is chosen from the group comprising tars or tar derivatives whose plasticizing properties have been demonstrated within the scope of the invention, such as coal tar, in the form of an extract or a solution of distillates, and derivatives thereof, namely cresol, phenol, sodium phenate, chloroxylenol, polyethoxylated alkylphenol and ethohexadiol, or tars produced from wood (birch, pine, soapbark, juniper etc.) and derivatives thereof, such as saponins, and also mineral oils or extracts or vegetable oils, such as cade oil, essential oil of birch, linseed oil, petroleum spirit, ichthammol and extracts of nettle, burdock root, pellitory, jamborandi, nasturtium, willow and Swertia Japonica. It has been found, surprisingly, that the incorporation of these agents into the matrix, despite their chemical complexity (in particular that of coal tar) in terms of the multitude of different active molecules, permits a satisfactory release as regards the clinical efficacy, compared with a traditional application of the same active agents. Other active substances, used by themselves or in association, are chosen from essential vegetable oils with antibacterial or antiinflammatory properties, such as thymol, menthol, terpineol and eucalyptol, in particular alpha-bisabolol.

Other active substances are the pyrithiones and derivatives thereof, for example pyrithione zinc, pyrion disulfide (RTM), ciclopirox and derivatives thereof, for example ciclopirox olamine, piroctone olamine or derivatives of alpha-thujaplicin or betathujaplicin, in particular copper salts or other agents with an antifungal action, such as: enilconazole, clotrinazole, miconazole, econazole, isoconazole, tolnaftate, pimaricin, nistatine and ketonazole.

Among other active substances which have given good results, mention must also be made of salicylic acid and its alkali metal derivatives, or methyl salicylate, as well as selenium sulfides, other sulfides, sulfur derivatives, sulfur, zinc sulfate, resorcinol, captan and undecylenic acid and derivatives thereof.

The invention can also be put into effect in a device which contains, as the active substance, by itself or in a mixture, benzoic acid and/or boric acid and derivatives thereof, such as sodium borate, as well as chlorhexidine and hexamidine.

Camphor, known in very small concentrations as a plasticizer for cellulose esters and ethers, can be incorporated in concentrations of the order of 5 to 15%. To improve its migration properties in the matrix, it is solubilized in an organic solvent before incorporation.

It is also possible to use dioxyanthranol and/or parahydroxybenzoate and/or benzocaine (ethyl aminobenzoate).

In another embodiment of the invention, the active substance is active in preventing the disorders due to ageing of the skin and/or the scalp, by combatting wrinkles and/or hair loss or by favoring fresh hair growth.

In this case, the active substance is chosen from synthetic plant or animal hormones such as estradiol, progesterone, cynosterone acetate and/or hydrocortisone and their derivatives, and/or vitamins of groups A, B, C, D, E, F, H and PP and their derivatives, i.e. panthothenic acid and its derivatives in the form of calcium and sodium salts, nicotinic acid and its derivatives in the form of ethyl or methyl nicotinate, paraaminobenzoic acid, pyridoxine and its hydrochloride, retinoic acid, riboflavin ($B_2$) and folic acid ($B_6$).

Good results have been obtained with certain vitamins, such as vitamins $B_6$, H, PP and C and panthenol, which are known for the importance of their action on the epithelium and superficial body growths and which it had hitherto been impossible to use satisfactorily because of their frequent instability and their selective stability, but which, surprisingly, can be incorporated in a macromolecular matrix, such as described above, by the process according to the invention. Vitamin F can be used not only for its plasticizing properties but also as a solvent and release promoter for vitamins A and E and their derivatives. Vitamin E possesses the dual advantage of having an inherent action on the hair and an antioxidant action for vitamins A and F when the manufacturing process is carried out.

Other agents which are active in preventing disorders due to ageing of the skin and/or the scalp and which can be used according to the invention are biological plant and animal extracts such as essential oils, colloidal oatmeal, wheatgerm oil, olive oil, ginseng extracts, placental extracts, amniotic fluid extracts, horsehair extracts, tissue extracts, lecithin or metabolic derivatives such as the allantoin of propolis.

Among the biological derivatives of animal origin, derivatives of the substances constituting the intercellular matrix of the dermis are of particular value in caring for the skin, the scalp and the hair. These are especially fractions of macromolecules: keratin, collagen, elastin, mucopolysaccharides, proteoglycans and glycoproteins of structures, as well as phospholipids and lipoamino acids. Macroprotein hydrolysates consist particularly of amino acids and certain sugars or derivatives, for example hydroxyproline, desmosin, N-acetylglucosamine, glucuronic acid, glucosamine, tryptophan and cysteine. Of these substances, DL-methionine, S-carboxymethylcysteine and glucuronic acid are of particular value in caring for the scalp, as are cystine and methylcysteine sebacate.

Particularly effective agents which are active in stimulating fresh hair growth are dichlorophene and diethanoldodecanamide, caproyl chloride, diphenhydramine hydrochloride, tetracaine hydrochloride and minoxidil and their derivatives, and dinitrochlorobenzene.

In another embodiment of the invention, the active substance is chosen especially for its cosmetic and hygienic properties from silicone oligomers, for example polydimethylsiloxane oligomer, silicone/glycol copolymers, cyclomethicones, amidomethicone, fatty acid derivatives such as their esters or polyesters, quaternary ammonium compounds such as their esters, alkanolamides, polyglycol esters, fatty alcohols or high-molecular alcohols and their derivatives such as fatty alcohol polyglycol ethers, or betaine derivatives such as coconut amidoethylbetaine or coconut oleamidopropylbetaine.

Some of these active agents are used in the field of plastics as internal lubricants (fatty alcohols or high-molecular alcohols and their derivatives) and external lubricants (fatty acids and derivatives), mold release agents (silicones) and antistatic agents (quaternary ammonium derivatives and betaine derivatives), for example, in small concentrations (of the order of 2%).

For hygienic or cleaning purposes, the active agent used is orris or lycopodium powder and/or any other agent which absorbs grease and/or has a detergent action. If the active agent is a powder which absorbs grease, its concentration in the matrix is between 15 and 30%.

According to the invention, the devices which are shown in FIGS. 1 to 3, but which can have different forms from those illustrated (for example, they can be in the form of hair styling instruments such as slides, curlers, rollers, pins, clips etc.), are shaped in totality or only in their active parts, whether these be the teeth of combs or brushes or the beads or the like of massaging articles, from the abovementioned ingredients by a process in which a dry powder is prepared by mixing one or more constituent polymers of the matrix, at a temperature of about 60°, with one or more active agents which have been micronized beforehand if they are in the solid form, or microsolubilized in a mixture of plasticizer and adjuvants, the said powder is left to cool and ingredients such as perfumes or the like are then added, and the device is shaped by molding or extrusion at a temperature of between 80° and 140° C. in a mold of appropriate shape.

The examples which follow illustrate other characteristics, advantages and special features of the invention.

I—DEVICES FOR ANTIDANDRUFF, ANTISEBORRHEA AND ANTIPSORIASIS TREATMENT:

The following compositions are prepared in parts by weight:

|  | EXAMPLES: | | | |
| --- | --- | --- | --- | --- |
|  | no. 1 | no. 2 | no. 3 | no. 4 |
| Pyrithione zinc (micronized and then microsolubilized in DBP) | 16% | | | |
| Octopirox (micronized and then microsolubilized in dioctyl adipate, DOA) | | 12% | | |
| Saponin-containing coal tar | | | 19% | 7% |
| Essential vegetable oils | 4% | 4% | | 2.5% |
| Epoxidized soya oil | 4% | 2.5% | 2% | 2% |
| Calcium stearate | 2.5% | 2.5% | 2% | 1.5% |
| Dioctyl adipate | 20% | | 6% | |
| Dibutyl phthalate | | 15% | | 11% |
| Silica | 4% | 6% | | |
| Butadiene/acrylonitrile | | | 2% | |
| PVC | 49.5% | 58% | 69% | 22.5% |
| Polyethylene | | | | 53.5% |

The above compositions are then shaped by molding at a temperature of the order of 95° C.

| EXAMPLES: | | | |
| --- | --- | --- | --- |
| no. 5 | | no. 6 | |
| Salicylic acid (micronized) | 15% | Coal tar (extract) Mineral oil | 14% 10% |

-continued

| EXAMPLES: | | | |
|---|---|---|---|
| no. 5 | | no. 6 | |
| Propylene glycol | 5% | Essential vegetable | 1% |
| DOA | 20% | oils | |
| Myristoleic acid | 1% | Zinc oxide | 5% |
| Millicarb | 8% | Stearic acid | 3% |
| Epoxidized soya oil | 2% | Sulfur | 2.5% |
| Calcium stearate | 2.5% | CBS | 0.8% |
| PVC | 46.5% | Clay | 20% |
| | | SBT rubber | 13.7% |

The composition of Example no. 5 is shaped at a relatively low temperature of the order of 80°–85° C. in order to allow for the fact that salicylic acid, which sublimes at 76° C., degrades rapidly on heating at atmospheric pressure.

The composition of Example no. 6, on the other hand, is shaped by means of a vulcanization treatment for 12 minutes at about 140° C.

EXAMPLES

No. 7

Compositions comparable to those of Example no. 5 were prepared using selenium sulfide and resorcinol and the said compositions were then shaped as indicated for the said example.

No. 8

Compositions comparable to those of Example no. 1 were prepared using undecylenic acid and zinc and/or sodium undecylenate.

The compositions were then shaped as described above with reference to Example no. 1.

No. 9

A composition comparable to that of Example no. 2 was prepared using ethohexadiol. The composition was then shaped as indicated in the said example.

| | EXAMPLES: | | |
|---|---|---|---|
| | no. 10 | no. 11 | no. 12 |
| Essential vegetable oils (⅓ menthol, ⅓ thymol, ⅓ eucalyptol) | 9% | 2% | |
| Saponin-containing coal tar | | 10% | 12% |
| Polyethylene | | | 90% |
| EVA | 91% | 88% | |

The compositions of Examples 10, 11 and 12 are shaped by molding at a temperature of the order of 95° C.

II—DEVICES FOR TREATMENT TO COMBAT HAIR LOSS OR FAVOR FRESH HAIR GROWTH:

The following compositions were prepared in parts by weight:

| | | EXAMPLES: | | |
|---|---|---|---|---|
| | | no. 13 | no. 14 | no. 15 |
| A | Vitamin A (acetate) | 3% | | |
| | Vitamin E | 2% | | |
| | Vitamin F | 12% | | |
| | Biotin (vitamin H) | | | 6% |
| | Cystine | | | 10% |
| | Essential vegetable oils | 2% | 1% | |
| | Thiamine hydrochloride | | 0.5% | |
| | Nicotinamide (vitamin PP) | | 0.9% | |
| | Panthenol | | 0.7% | |
| B | Vitamin C | | 0.1% | |
| | Glycerol | | 10% | |
| C | Epoxidized soya oil | 2% | 2% | 3% |
| | Calcium stearate | | 3% | 2% |
| | Dioctyl adipate (DOA) | | | 25% |
| | Dibutyl phthalate | 15% | 24% | |
| | Colorant | 0.3% | 0.3% | |
| D | Butadiene/acrylonitrile | 2% | 5% | |
| | Polyvinyl chloride | 59.5% | 52.5% | 54% |

To shape the products from the above compositions, mixture A is solubilized in the glycerol, in the case of Example 14, and the whole is mixed with composition C, whereas composition A on its own is mixed with the said composition C in the case of Examples 13 and 15. The whole is advantageously microsolubilized before being mixed with D.

For Examples 13 and 14, glycerol and vitamin F are used as a solvent for the active agents and a potentiator for their release, respectively.

The manufacturing process takes place as indicated above for Examples 1 to 4.

Agents whose function is to favor the passage of the active agents through the scalp can advantageously be included in the active substance, examples being alkyl sulfoxides (DMSO), dimethylacetamide, dimethylformamide, pyrrolidone and derivatives (Azone RTM) and N,N-diethyl-m-toluamide.

Surprisingly, it is found that, under the conditions of the invention, the degree of degradation of the vitamins is very low during manufacture and that they subsequently benefit from protection by virtue of their inclusion in the matrix, which protects them from light and moisture (the surface of the polymer is hydrophobic) and also from pH variations (the pH in the matrix must be between about 3 and 6).

The following compositions are prepared in parts by weight:

| | EXAMPLES: | | | |
|---|---|---|---|---|
| | no. 16 | no. 17 | no. 18 | no. 19 |
| Vegetable oil (containing cyprosterone acetate in saturated solution) | 25% | | | |
| Nicotinic acid (solubilized in propylene glycol) | | 3% | | |
| | | 8% | | |
| TWIN 80 (RTM) | | 12% | | |
| Cade oil | | | 3% | |
| Camomile extracts | | | 5% | |
| Thujaplicin | | | | 7% |
| Oil of menthol | | | | 4% |
| Caproyl chloride | | | | 5% |
| DBP | 12% | 7% | 25% | 22% |
| Epoxidized soya oil | 3% | 2% | 3% | 4% |
| Calcium stearate | 2% | 2% | 2% | 2% |
| PVC | 58% | 66% | 62% | 56% |

The compositions of Examples 16 to 19 are shaped by molding at a temperature of 95° C.

EXAMPLE no. 20

Compositions comparable to those of Example 17 were prepared using phospholipids, lipoamino acids or fatty acid ester polyols as active agents and the said compositions were shaped as described in the said example.

EXAMPLE no. 21

Compositions comparable to those of Example no. 18 were prepared using liposoluble extracts of nasturtium, nettle, cinchona, henna or oatmilk, or liposoluble extracts of animal origin from tissue, blood, placenta, amniotic fluid, horeshair, fish oils or lecithin, and the said compositions were then shaped as indicated in Example 18.

EXAMPLE no. 22

Compositions comparable to those of Examples 1 and 15 were prepared using DL-methionine, S-carboxymethylcysteine or gluconic acid as the active agent and the said compositions were then shaped as indicated in the said examples.

EXAMPLE no. 23

Compositions comparable to those of Examples 13 and 17 were prepared using, as the active agent for conditioning the hair, silicone oligomers, fatty acid esters and polyesters, high-molecular alcohols and their derivatives, quaternary ammonium derivatives and betaine derivatives, and the said compositions were then shaped as described with reference to the said examples.

There now follows a description of the results of experiments intended to illustrate the process for using the devices according to the invention.

COMPARATIVE TREATMENT EXPERIMENTS

Experiment no. 1

The purpose of the experiment is to compare the clinical efficacy of a commercial shampoo containing coal tar with that of a coal tar brush according to the present invention. The brushes used for carrying out the experiment are square in shape, with a side length of 8.7 cm, composed entirely of the macromolecular polymer matrix containing the active substance, and having about 225 spikes of 0.75 cm in length on one of the faces.

The experiment was conducted on 60 people (3 groups of 20) who had been suffering from psoriasis of the scalp for more than 3 months, the average duration of the complaint being 1.1 years (±0.15). Three groups were selected to be as homogeneous as possible from the point of view of the duration and extent of the scalp complaint. Group A had to wash their hair once every three days with a placebo shampoo and brush their hair twice a day with the active brush. Group B had to adopt the following protocol: washing their hair once every three days with the coal tar shampoo and brushing twice a day with a placebo brush.

Group C used only the placebos in accordance with the same protocol.

Two parameters were followed throughout the experiment: the degree of desquamation and the greasy condition of the scalp, on days 30 and 60 of the treatment. No other scalp treatment was administered during the experiment.

The results are given in the table below:

|  | Group A | | Group B | | Group C | |
| --- | --- | --- | --- | --- | --- | --- |
|  | 30 d | 60 d | 30 d | 60 d | 30 d | 60 d |
| Greasy condition | | | | | | |
| better | 3 | 10 | 4 | 6 | 3 | 1 |
| worse | 2 | 0 | 1 | 0 | 7 | 11 |
| no change | 15 | 10 | 15 | 14 | 10 | 8 |
| Desquamation | | | | | | |
| better | 9 | 13 | 13 | 12 | 2 | 0 |
| worse | 4 | 3 | 3 | 3 | 8 | 4 |
| no change | 7 | 4 | 4 | 5 | 10 | 16 |

Experiment no. 2

In accordance with an identical protocol to that of the previous experiment, the action of a pyrithione zinc brush was compared with that of a commercial pyrithione zinc shampoo. The parameter studied is the presence of dandruff.

The results are given in the table below:

|  | Active shampoo Placebo brush | | Placebo shampoo Active brush | | Placebo shampoo and brush | |
| --- | --- | --- | --- | --- | --- | --- |
|  | 30 d | 60 d | 30 d | 60 d | 30 d | 60 d |
| No dandruff | 9 | 15 | 4 | 14 | 2 | 4 |
| better | 3 | 4 | 8 | 4 | 3 | 2 |
| worse | 1 | 0 | 0 | 0 | 7 | 6 |
| no change | 7 | 1 | 8 | 2 | 8 | 8 |

Experiment no. 3

Antidandruff Treatment

The purpose of the experiment was to compare the efficacy of a commercial shampoo containing pyrion disulfide with that of a brush according to Example 1 in which the pyrithione zinc had been replaced by pyrion disulfide. The brush is square in shape (side length of 8.7 cm), is composed entirely of the active polymer matrix and has 225 spikes of 0.75 cm in length on one of the faces.

The experiment was conducted on 60 people (3 groups of 20, pathologically homogeneous) who had been suffering from hyperseborrhea of the scalp and dandruff for more than 6 weeks. Group A washed their hair every 3 days with a placebo shampoo and styled their hair twice a day with the active brush. Group B used a pyrion disulfide shampoo every 3 days and styled their hair twice a day with a placebo brush. Group C used only the placebos in accordance with the same protocol. The parameter checked is the presence of dandruff:

|  | Group A | | Group B | | Group C | |
| --- | --- | --- | --- | --- | --- | --- |
|  | 30 d | 60 d | 30 d | 60 d | 30 d | 60 d |
| No dandruff (absence of dandruff) | 9 | 16 | 4 | 11 | 4 | 3 |
| better | 10 | 3 | 7 | 6 | 2 | 1 |
| worse | 0 | 0 | 1 | 0 | 5 | 7 |
| no change | 1 | 1 | 8 | 3 | 9 | 9 |

Experiment no. 4

Treatment of Wrinkles

The purpose of the experiment was to assess the activity of the device described in Example no. 13 in the treatment of wrinkles on the face. The active matrix was in the shape of a roller rotating around a spindle. The protocol consisted in massaging the wrinkled areas twice a day by rolling the device over them. The experiment was conducted on 10 women in the region of the cheek bones for 4 weeks. The results, obtained by analysis of macrophotographs of counter-impressions of the skin in three dimensions, showed an average reduction in visible wrinkles of 29%, ranging up to 38% in certain cases.

Experiment no. 5

Treatment of Hair Loss

The purpose of the experiment was to assess the activity of the device according to Example 17 in treating alopecia of the scalp. It was carried out on a group of 60 patients (including 20 of the female sex), all of whom had been followed up for more than a year and who, after having derived some benefit from conventional treatments, had found their condition stabilizing with large areas of alopecia persisting.

The device was used by half the patients (group A), who were divided into two groups homogeneous in terms of pathologies and areas, at a minimum rate of two brushings of the scalp and hair per day for 4 months. Group B used a lotion containing the same active agents, applied every other evening for 40 days and then applied at a rate of twice a week for 80 days.

Among the women, all the cases of alopecia were of the seborrheic type with distinct thinning in the region of the crown and temporofrontal regions. Among the men, all the chosen cases suffered from alopecia with thinning of the toupet and incipient alopecia in the region of the tonsure.

| Results: | | | | |
| --- | --- | --- | --- | --- |
| Total response of normal hair | | A | | |
| Partial response of normal hair (decrease in the thin areas) | | B | | |
| Partial response of fine hair | | C | | |
| No visible result (failure) | | D | | |
| | A | B | C | D |
| Group A | | | | |
| Men | 0 | 2 | 15 | 3 |
| Women | 3 | 3 | 4 | 0 |
| Group B | | | | |
| Men | 0 | 0 | 12 | 8 |
| Women | 1 | 2 | 5 | 2 |

What is claimed is:

1. A device for treating the external human epithelium, comprising a rigid macromolecular matrix, incorporating throughout at least one active substance chosen for its treatment action and for its migration characteristics within said matrix, said matrix being sufficiently rigid so as to fail to conform its shape to that of a desired area when contacting said desired area by brushing or combing, said active substance being applied to the desired area responsive to brushing or combing;
    said migration characteristics of said active substance including release of said active substance at the surface of said device when rubbed, causing said surface to become depleted of said active substance; and migration of said active substance within said matrix from beneath said surface to said surface;
    said device being produced by preparing a dry powder by mixing one or more constituent polymers of the matrix at a temperature of about 60° C., said at least one active agent being micronized prior to mixing, if in the solid form, or microsolubilized in a mixture of plasticizer and adjuvants, leaving said powder to cool down and shaping the device by molding or extruding at a temperature of between 80° and 140° C.

2. A device in accordance with claim 1, wherein said device takes the form of a comb or brush said comb or brush further comprising a frame, within the macromolecular matrix, which increases the strength of the device.

3. The device as claimed in claim 1, further comprising a handle made of another material than that of said macromolecular matrix, and means for attaching said handle to said macromolecular matrix.

4. The device as claimed in claim 1, wherein said active substance comprises at least one therapeutic agent for treatment of facial wrinkles.

5. The device as claimed in claim 1, wherein the active substance contains at least one agent which is therapeutically effective for treating hyperseborrhea, psoriasis, hair loss or dandruff or for assisting fresh hair growth.

6. The device as claimed in claim 1, wherein the active substance contains at least one cosmetically active agent for modifying hair.

7. The device as claimed in claim 1, wherein the active substance acts as a plasticizer for the macromolecular matrix.

8. The device as claimed in claim 1, wherein the active substance contains at least one vitamin and an unsaturated fatty acid.

9. The device as claimed in claim 1, wherein the active substance contains from 1 to 25% of plant extracts, animal extracts or essential oils.

10. The device as claimed in claim 1, wherein the active substance contains at least one ingredient for altering the rate of transcutaneous passage of the active agent.

11. The device as claimed in claim 5, wherein the matrix contains from 3 to 25% of pyrithione or its derivatives as the active agent.

12. The device as claimed in claim 5, wherein the matrix contains from 1 to 25% of coal tar or its derivatives as the active agent.

13. The device as claimed in claim 5, wherein the active substance includes: at least a grease absorber selected from the group consisting of orris and lycopodium powder; a detergent; silicone oligomers; fatty acid derivatives; and quaternary ammonium compounds.

14. The device as claimed in claim 1, wherein the matrix is made from molded, extruded or cast polymer selected from the group consisting of polyethylene, polyurethane, polyvinylchloride and mixtures thereof.

15. The device as claimed in claim 14, wherein matrix contains between 0 and 25% plasticizer by weight of the matrix, the polymer or mixture of polymers being about 45 to 90% by weight and the active substance being from 2 to 25% by weight.

16. A process for applying to a desired area of the external human epithelium, at least one active substance, comprising the steps of repeatedly and intermittently contacting said area to be treated with a device comprising a rigid macromolecular matrix, which fails to conform its shape to that of said desired area when contacting said desired area by brushing or combing, and which is sufficiently rigid to disentangle human hair, brushing or combing said desired area to release the active substance to the desired area, said rigid macromolecular matrix having said active substance incorporated throughout, said active substance being chosen for its migration characteristics, said migration characteristics including release of said active substance at the surface of said device when rubbed, causing said surface to become depleted of said active substance, and migration of said active substance within said matrix and beneath said surface to said surface, said device being produced by preparing a dry powder by mixing one or more constituent polymers of the matrix at a temperature of about 60° C., said at least one active agent being micronized prior to mixing if in the solid form, or microsolubilized in a mixture of plasticizer and adjuvants, leaving said powder to cool down and shaping the device by molding or extruding at a temperature of between 80° and 140° C., said contacting of said rigid macromolecular matrix against said desired area releasing said active substance, whereby said active substance is deposited on said desired area.

17. A device according to claim 1 in the form of a brush molded of polyvinylchloride, said active substance comprising a mixture of a quaternary ammonium compound and coal tar.

* * * * *